United States Patent
Hallewell et al.

(10) Patent No.: US 6,830,906 B2
(45) Date of Patent: Dec. 14, 2004

(54) MANGANESE SUPEROXIDE DISMUTASE CLONING AND EXPRESSION IN MICROOGANISMS

(75) Inventors: Robert Alexander Hallewell, San Francisco, CA (US); Graeme Ian Bell, San Francisco, CA (US); Guy Towns Mullenbach, Oakland, CA (US)

(73) Assignee: Chiron Corporation, Emeryville, CA (US)

(*) Notice: Subject to any disclaimer, the term of this patent is extended or adjusted under 35 U.S.C. 154(b) by 52 days.

(21) Appl. No.: 09/878,589

(22) Filed: Jun. 11, 2001

(65) Prior Publication Data

US 2002/0081287 A1 Jun. 27, 2002

Related U.S. Application Data

(62) Division of application No. 06/918,534, filed on Oct. 14, 1986, now Pat. No. 6,326,003.

(51) Int. Cl.[7] ............................ C12N 9/02; C12N 1/20; C12N 1/14
(52) U.S. Cl. .............. 435/189; 435/252.33; 435/254.21
(58) Field of Search .......................... 435/189, 252.33, 435/254.21

(56) References Cited

U.S. PATENT DOCUMENTS

| | | |
|---|---|---|
| 5,246,847 A | 9/1993 | Hartman et al. |
| 6,326,003 B1 * | 12/2001 | Hallewell et al. .......... 424/94.4 |

FOREIGN PATENT DOCUMENTS

| | | |
|---|---|---|
| DE | 2 183658 A | 10/1987 |
| EP | 0 230360 0 9 | 2/1983 |
| EP | 5 11056 | 2/1986 |
| EP | 0 284105 | 2/1988 |
| EP | 0 282899 | 9/1988 |
| EP | 1 0488059 | 9/1988 |

OTHER PUBLICATIONS

Beck Y. et al. Human Mn superoxide dismutase cDNA sequence, Nucleic Acid Res. (1987), 15, 9076.*
Xiang K. et al. Multiple Taq 1 RFLPs at the human mangenese superoxide dismutase (SOD2) locus on chromosome 6, Nucleic Acid Res. (1987), 15, 7654.*
Bannister J. V. et al. Isolation and Characterization of Superoxide Dismutase, Mehtods in Enzymology, 1984, 105, 88–93.*
Borgstahl G. E. et al. The Structure of Human Mitochondrial Manganese Superoxide Dismutase Reveals a Novel Tetrameric Interface of Two 4–Helix Bundles, Cell, 1992, 71, 107–118.*
Wispe J. R. et al. Synthesis and processing of the precursor for human mangano–superoxide dismutase Biochim. Biophys. Acta, 1989, 994(1), 30–36.*
Barra et al., *FEBS Letters* 120(1):53–55 (1980).
Barra et al., *J. Biol. Chem.* 259(20):12595 (1984).
Carlioz et al., *EMBO J.* 5(3):623–630 (1986).
Flohe et al., *Developments in Biochemistry* (Eds. E.M. Bannister and J. V. Bannister), Elsevier/North Holland, Amsterdam 11B:424–430 (1980).
Hallewell et al., *Nucleic Acids Research* 13(6):2017–2034 (1985).
Jabusch et al., *Biochemistry* 19:2310–2316 (1980).
Lieman–Hurwitz et al., *Proc. Natl. Acad. Sci. U.S.A.* 79:2808–2811 (1982).
Steiman et al., *J. Biol. Chem.* 249(22):7326–7338 (1974).
Tsunasawa et al., *J. Biol. Chem.* 260(9):5382–5391 (1985).
Wilsman, Superoxide and Superoxide Dismutase in Chemistry, Biology, and Medicine, Porceedings of the 4th International Conference on Superoxide and Superoxide Dismutase held in Rome, Italy, Sep. 1–6, 1985, (Elsevier Publishers, edited by Guiseppe Rotilio), pp. 500–507 (1986).

* cited by examiner

*Primary Examiner*—Rebecca E. Prouty
*Assistant Examiner*—Malgorzata A. Walicka
(74) *Attorney, Agent, or Firm*—Roberta L. Robins; Lisa E. Alexander; Robert P. Blackburn

(57) ABSTRACT

Methods and compositions are provided for the production of human manganese superoxide dismutase and a protocol for enhancing efficiency of expression. The gene encoding for human manganese superoxide dismutase was isolated and inserted into a vector in conjunction with a synthetic linker which provides for enhanced efficiency in translation.

*E. coli* strain HB101 containing the plasmid Nco5AHSODm was deposited at the A.T.C.C. on Oct. 3, 1986 and given Accession No. 67191.

5 Claims, 7 Drawing Sheets

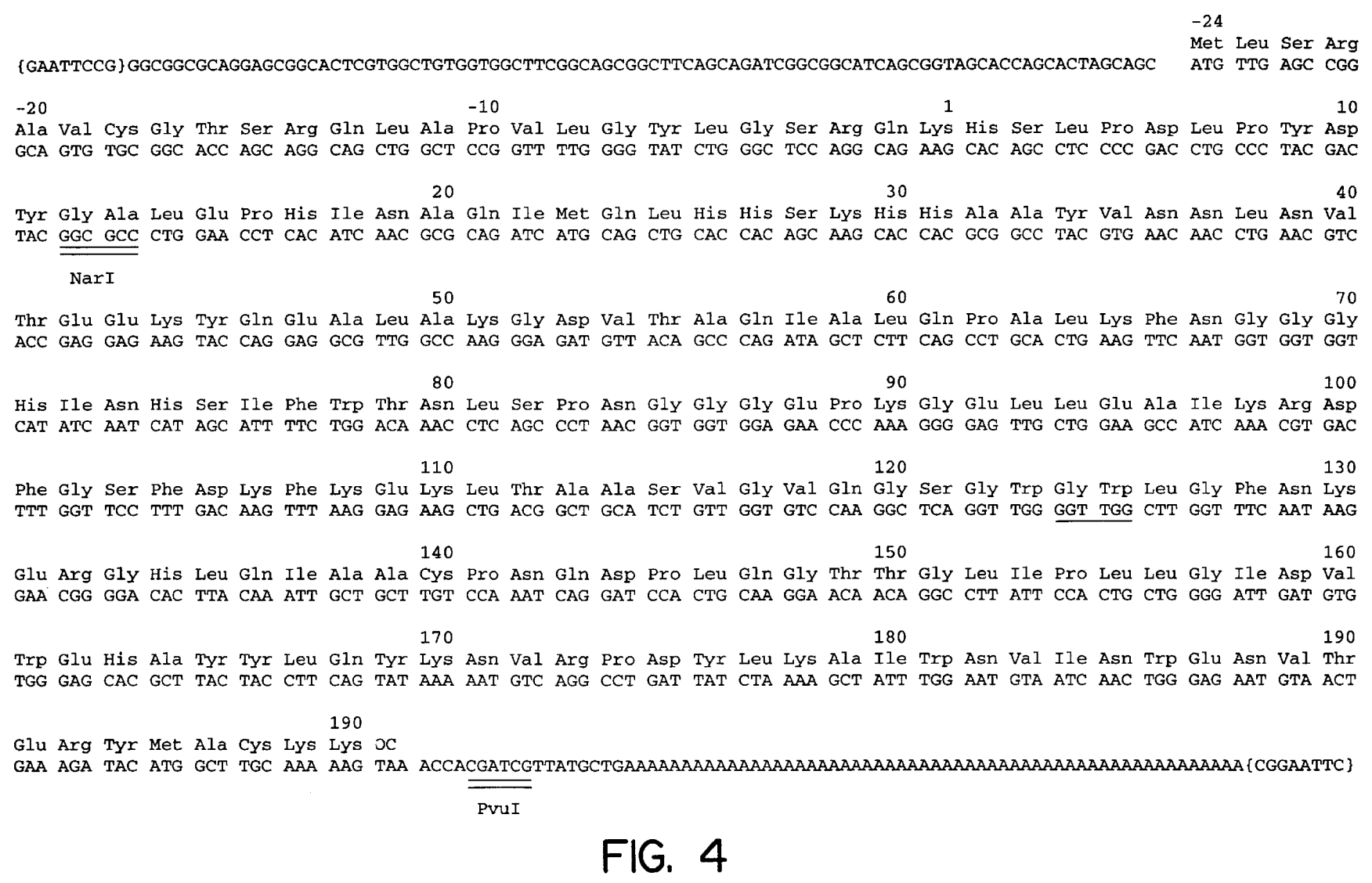

```
(GAATTCCG)GGCGGCGCAGGAGCGGCACTCGTGGTCGTGGTGGCTTCGGCAGCAGATCGGCGCATCAGCGGTAGCACCAGCACTAGCAGC
                                                                                          -24
                                                                                          Met Leu Ser Arg
                                                                                          ATG TTG AGC CGG
         -20                                -10                          1                               10
Ala Val Cys Gly Thr Ser Arg Gln Leu Ala Pro Val Leu Gly Tyr Leu Gly Ser Arg Gln Lys His Ala Ala Tyr Leu Pro Asp Leu Pro Tyr Asp
GCA GTG TGC GGC ACC AGC AGG CAG CTG GCT CCG GTT TTG GGG TAT CTG GGC AGG CAG AAG CAC AGC GCG CTC CCC GAC CTG CCC TAC GAC
                                              20                          30                             40
Tyr Gly Ala Leu Glu Pro His Ile Asn Ala Gln Ile Met Gln Leu His Ser Lys His His Ala Ala Tyr Val Asn Asn Leu Asn Val
TAC GGC GCC CTG GAA CCT CAC ATC AAC GCG CAG ATC ATG CAG CTG CAC AGC AAG CAC CAC GCG GCC TAC GTG AAC AAC CTG AAC GTC
     NarI
         50                                60                           70
Thr Glu Lys Tyr Gln Glu Ala Leu Ala Lys Gly Asp Val Thr Ala Gln Ile Ala Leu Gln Pro Ala Leu Lys Phe Asn Gly Gly Gly
ACC GAG AAG TAC CAG GAG GCG TTG GCC AAG GGA GAT GTT ACA GCC CAG ATA GCT CTT CAG CCT GCA CTG AAG TTC AAT GGT GGT GGT
                                              80                          90                            100
His Ile Asn His Ser Ile Phe Trp Thr Asn Leu Ser Pro Asn Gly Gly Gly Glu Pro Lys Gly Glu Leu Leu Glu Ala Ile Lys Arg Asp
CAT ATC AAT CAT AGC ATT TTC TGG ACA AAC CTC AGC CCT AAC GGT GGT GGA GAA CCC AAA GGG GAG TTG CTG GAA GCC ATC AAA CGT GAC
        110                              120                          130
Phe Gly Ser Phe Asp Lys Phe Lys Glu Lys Leu Thr Ala Ala Ser Val Gly Val Gln Gly Ser Gly Trp Gly Phe Leu Gly Phe Asn Lys
TTT GGT TCC TTT GAC AAG TTT AAG GAG CTG ACG GCT GCA TCT GTT GGT GTC CAA GGC TCA GGT TGG GGT TTC CTT GGT TTC AAT AAG
                                           140                          150                          160
Glu Arg Gly His Leu Gln Ile Ala Ala Cys Pro Asn Gln Asp Pro Leu Gln Gly Thr Thr Gly Leu Ile Pro Leu Leu Gly Ile Asp Val
GAA CGG GGA CAC CTT CAA ATT GCT GCT TGT CCA AAT CAG GAT CCA CTG CAA GGA ACA ACA GGC CTT ATT CCA CTG CTG GGG ATT GAT GTG
        170                                                180                              190
Trp Glu His Ala Tyr Tyr Leu Gln Tyr Lys Asn Val Arg Pro Asp Tyr Leu Lys Ala Ile Trp Asn Val Ile Asn Trp Glu Asn Val Thr
TGG GAG CAC GCT TAC TAC CTT CAG TAC AAA AAT GTC AGG CCT GAT TAT CTA AAA GCT ATT TGG AAT GTA ATC AAC TGG GAG AAT GTA ACT
                     190
Glu Arg Tyr Met Ala Cys Lys Lys OC
GAA AGA TAC ATG GCT TGC AAA AAG TAA ACCACGATCGTTATGCTGAAAAAAAAAAAAAAAAAAAAAAAAAAAAAAAAAAAAAAAAAAAAAAAAAAA(CGGAATTC)
                                                        PvuI
```

FIG. 4

MANGANESE SUPEROXIDE DISMUTASE CLONING AND EXPRESSION IN MICROOGANISMS

This application is a divisional of U.S. Patent Application Ser. No. 06/918,534, filed Oct. 14, 1986, now U.S. Pat. No. 6,326,003, from which application priority is claimed pursuant to 35 U.S.C. §120, and which application is incorporated herein by reference in its entirety.

BACKGROUND OF THE INVENTION

FIELD OF THE INVENTION

The production of the enzyme manganese human superoxide dismutase (hSODm) by recombinant DNA techniques is described. Both natural and modified enzymes are produced utilizing novel DNA constructs, plasmids and transformed microbial expression systems.

Superoxide dismutase ("SOD") is in fact a variety of different enzymes found in most living organisms. One function in mammals is to destroy superoxide. Superoxide is a material naturally produced during phagocytosis and aerobic metabolism. The superoxide dismutases are characterized in families based on the metal ion associated with the enzyme, where the ions can be iron, manganese, copper, and copper and zinc. Superoxide dismutase, e.g., from bovine liver, has found clinical use, particularly as an anti-inflammatory agent in mammals including humans and to decrease tissue injury due to reperfusion (post-ischemic). Other utilities include scavenging superoxide anions due to exposure of a host to various superoxide-inducing agents, e.g. radiation, paraquat, etc.; prophylaxis or therapy for certain degenerative diseases, e.g., emphysema; food preservation; and the like.

It is therefore important that stable supplies of physiologically acceptable superoxide dismutase be made available, particularly for use in vivo as an anti-inflammatory agent or for other therapeutic purposes. For human application it would be preferable to employ the homologous enzyme to prevent or minimize possible immune response. By employing recombinant DNA techniques, there is the opportunity to produce products efficiently, which have the desired biological activities of superoxide dismutase, such as immunological and enzymatic activities.

Description of Relevant Publications

The primary structure of human liver manganese superoxide dismutase was described by Barra et al., *J. B. C.*, 259:12595–12601, (1984). Either bacterial iron superoxide dismutase (FeSOD) or bacterial manganese superoxide dismutase (MnSOD) were shown to be required as a defense against oxygen toxicity by Carlioz et al., EMBO Journal, 5:623–630, (1986). The amino-terminal processing of methionine by yeast was shown by Tsunasawa et al., J.B.C., 260:5382–5391, (1985). Human copper/zinc superoxide dismutase was described by Hallewell, et al., Nucleic Acids Research, 13:2017–2034, (1985). A superoxide dismutase produced in Serratia marcescens is described in EPO application 0172577. An immobilized superoxide dismutase was described in EPO application 070656.

The amino acid sequence of human erythrocyte Cu—Zn superoxide dismutase was described in Jabusch et al., *Biochemistry* (1980) 19:2310–2316 and Barra et al., *FEBS Letters* (1980) 120:53–55. Bovine erythrocyte Cu—Zn SOD was described by Steinman et al., *J. Biol. Chem.* (1974) 249:7326–7338. A SOD-1 (Cu—Zn SOD) cDNA clone is described by Lieman-Hurwitz et al., *Proc. Natl. Acad. Sci. USA* (1982) 79:2808–2811.

SUMMARY OF THE INVENTION

Novel compositions are provided comprising nucleic acid sequences for the expression of polypeptides exhibiting the biological properties of human manganese superoxide dismutase ("hSODm"). Also provided are methods for producing such polypeptides employing recombinant DNA techniques and microorganism hosts. The subject polypeptides find use in vivo and in vitro in destroying superoxide.

Also provided is a novel modified hSODm. A modified DNA coding for hSODm with the first two amino acids, lysine and histidine, removed, resulted in a polypeptide with the third amino acid, serine, positioned adjacent to the translation initiating amino acid methionine. This modified hSODm permitted removal of the amino terminal methionine by processing enzymes.

A method of treating a patient having inflammatory joint disease or post-ischemic tissue injury is also provided.

BRIEF DESCRIPTION OF THE DRAWINGS

FIG. 4 indicates the sequence of both the coding strand of hSODm cDNA (5'–3') and the amino acid sequence of the hSODm translation product with signal sequence.

DESCRIPTION OF SPECIFIC EMBODIMENTS

Figure 1A:
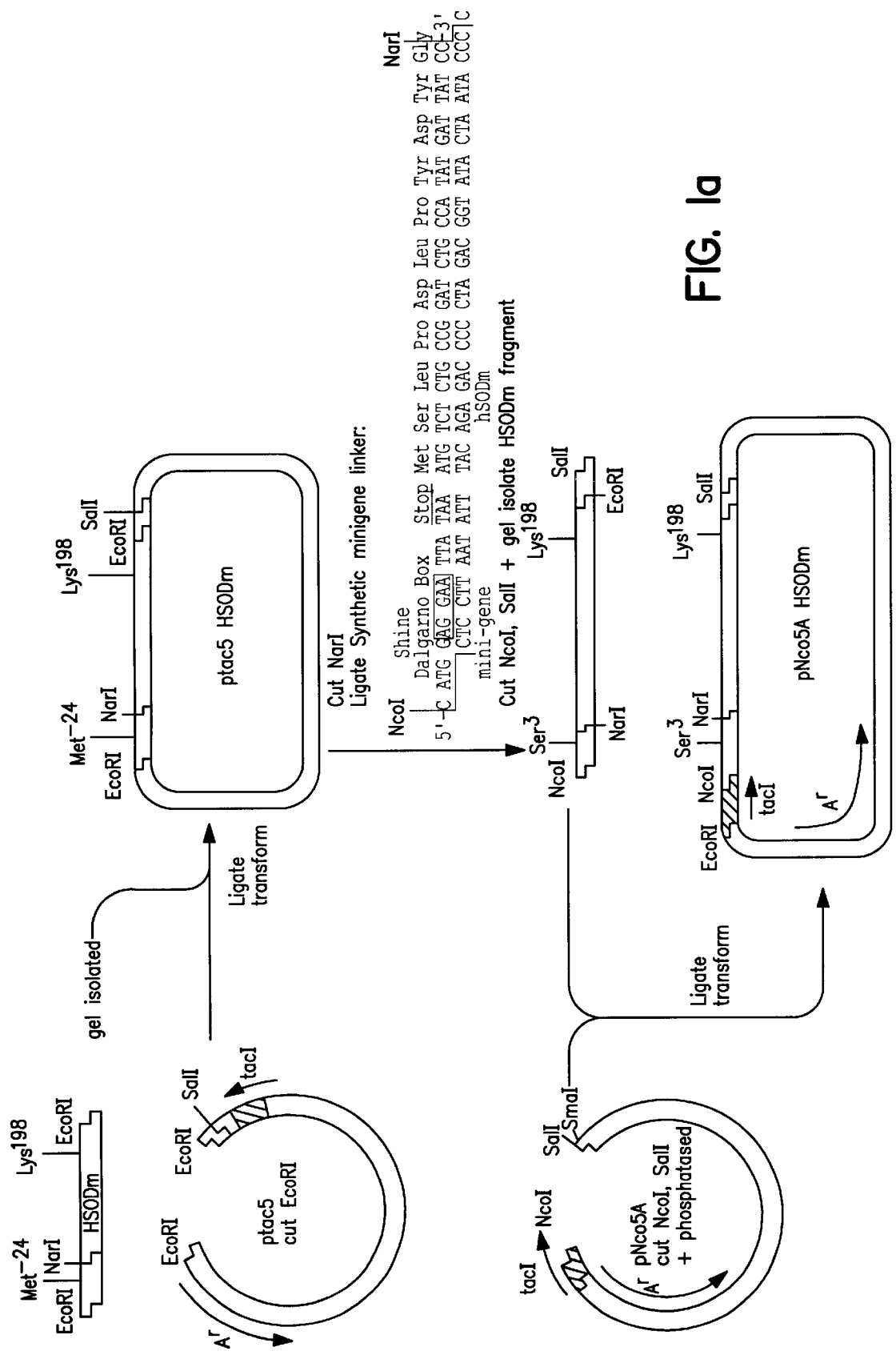
FIGS. 1*a* and 1*b* are a flow chart describing the construction of pNco5AhSODm, a bacterial expression plasmid for hSODm.

Methods and compositions are provided for the efficient expression of polypeptides demonstrating the biological activities of human manganese superoxide dismutase ("hSODm"). The methods employ a DNA sequence ("hSODm gene") encoding at least a substantial portion or all of the amino acid sequence of hSODm in conjunction with a transcriptional initiation regulatory region providing for efficient expression in the expression host. The hSODm gene is inserted into an appropriate vector for expression in a host, conveniently under conditions which allow for processing to remove the N-terminal methionine.

It is possible to modify the 5'-end of the structural gene to remove one or both of the first two amino acids of the mature polypeptide. Such modification may be accomplished by a variety of conventional methods. For example, the structural gene may be restricted near its 5'-end to remove a known number of nucleotides. A synthetic oligonucleotide (adapter) may then be joined to the cohesive end remaining after restriction. The oligonucleotide will restore and substitute the base pairs as necessary to provide the desired amino acid sequence. Alternatively, site-specific mutagenesis employing, e.g., phage M13, or primer repair can be used to effect an appropriate modification to the 5'-end of the structural gene.

In order to prepare hSODm, it is necessary to have a DNA sequence which encodes for hSODm. One manner of achieving such sequence is to clone cDNA from messenger RNA from cells which produce hSODm. Conveniently, human kidney cells may be used for this purpose. After the cDNA is cloned, where the DNA coding sequence is unknown, but at least a partial amino acid sequence is known, one may then screen the cDNA with mixtures of complementary synthetic DNA probes having all, or substantially all, of the possible variations of nucleotides encoding for the particular series of amino acid residues. The choice of the oligopeptide fragment for which the sequence encodes is somewhat arbitrary, although the fragment chosen will usually be selected to minimize the number of different sequences which must be synthesized. Two or more such probes hybridizing with the two ends of the hSODm cDNA may be used to select for those sequences containing all or substantially all of the coding sequence.

For hSODm, conveniently a DNA sequence encoding for the amino acid residues 197 to 211 can be used, particularly a probe having at least about 15 bases and not more than about 60 bases, more conveniently about 44 bases. With the probe in place one may then use restriction enzymes to digest the clones which appear to hybridize with the labeled probes, fractionate the DNA fragments and repeat the hybridization, particularly by employing a second series of probes which hybridize to DNA sequences encoding for a different series of amino acid residues in hSODm. Conveniently, these amino acid residues may be 23 to 27. Such probes are shown in Example I. One or more clones may be found which are positive to both probes and these may be used as a source for cDNA encoding for at least a substantial proportion of hSODm.

Quite surprisingly, it was found that the amino acid sequence which had been published for hSODm differed from the amino acid sequence encoded for by the cDNA. Specifically, two amino acids in positions 124 and 125 differed. Barra et al. disclosed the sequence of the mature protein including a leucine 124 and a glycine 125, while, the cDNA coded for glycine 124 and a tryptophan 125.

An mRNA source of human manganese superoxide dismutase cDNA can be isolated from any human cell producing manganese superoxide dismutase, for example kidney cells. However, one convenient source of such cDNA is the human kidney cell libraries wherein the entire mRNA has been converted to cDNA and inserted into lambda bacterial phage (λgt10). (Huynh et al., 1985). Individual specific clones can be selected using a primer which selects the particular clone containing the hSODm cDNA. Selection is by hybridizing with oligonulceotide probes that have been synthesized based on known amino acid sequences. The sequences of the probes were produced based upon the amino acid sequence of Barra et al., 1984, (supra). The sequence of DNA oligonucleotides illustrated in FIG. 4 codes for the entire amino acid sequence of the human manganese superoxide dismutase plus the 24 amino acid signal sequence which is normally removed during transfer of the nascent protein from the cytoplasm to the mitochondria. Based upon this DNA sequence, the correct amino acid sequence for the hSODm was determined. As previously discussed there were two amino acids, glycine 124 and tryptophan 125 that were previously unknown.

Bacterial expression vectors may be constructed by inserting either the entire hSODm cDNA or the modified hSODm cDNA coding for hSODm with the first two amino acids removed. Any bacterial expression system may be used with these DNA constructs. A preferred plasmid expression system is the plasmid pNco5A. In one embodiment the hSODm cDNA was inserted after a mini-gene which coded for 4 amino acids. This mini-gene was located such that it occurred in a Shine-Dalgarno region and provided the proper sequence for the Shine-Dalgarno region. The translation of the mini-gene thereby facilitated improved translation of the hSODm gene.

Figure 1B:
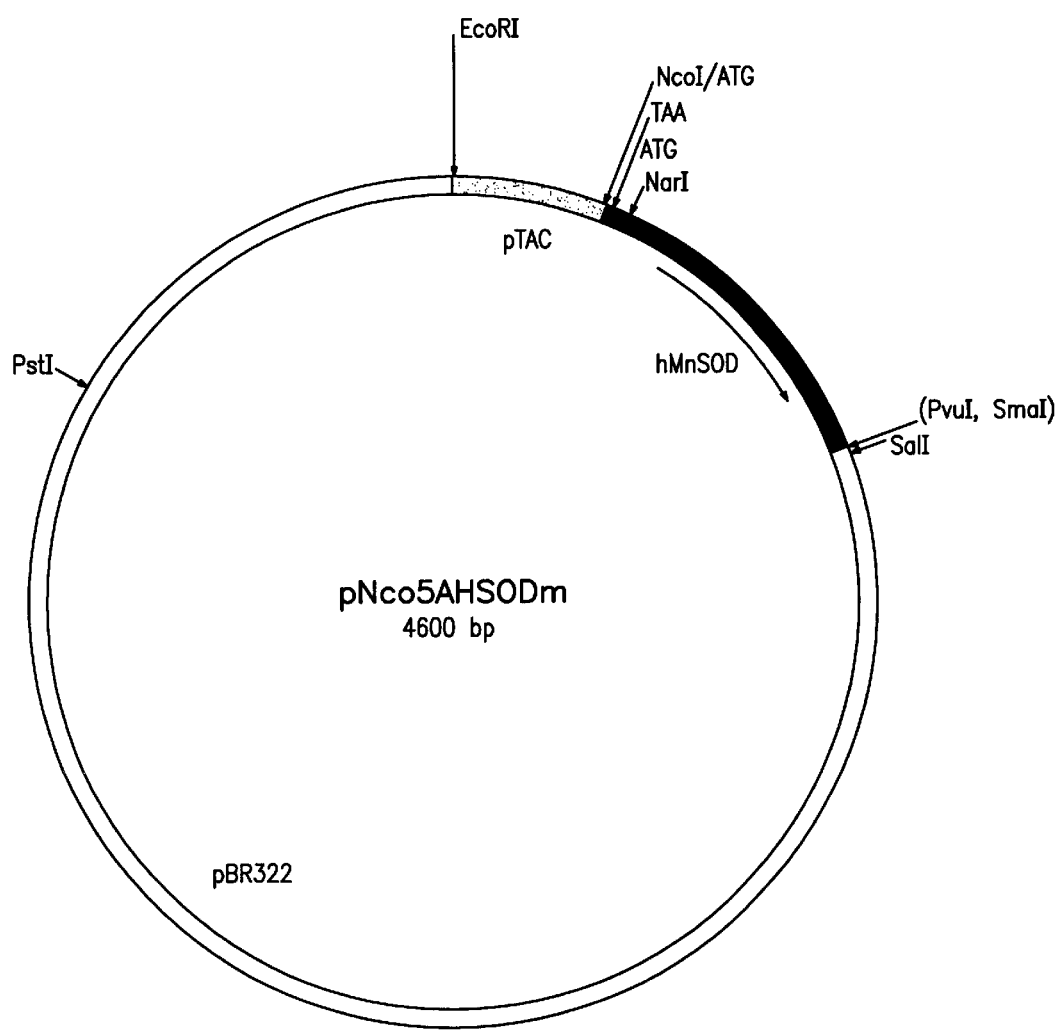

The preferred expression plasmid pNco5AhSODm was constructed using a synthetic linker described in FIG. 1. This linker incorporates in the same sequence both the Shine-Dalgarno region and a mini-gene terminating in a stop codon joined to the met codon of the modified hSODm. For the construction of the modified hSODm expression system, the codons for the two initial amino acids (Lys and His) were deleted. As a result, the initiation codon (Met) was located adjacent to the third amino acid (Ser) of the hSODm. The processing enzymes found in bacteria and yeast recognize a methionine adjacent to a serine and remove it as described by Tsunasawa et al., JBC 260:5382–5391 (1985) yielding a mature protein free from N-terminal methionine. This processing does not occur if the methionine is next to lysine or histidine (the first and second residues of HSODm). The serine adjacent to the initiating methionine in the hSODm polypeptide may also be replaced by any one of the following amino acids: alanine, glycine, proline, threonine, and valine. Any of these amino acids adjacent to the initiating methionine will result in a hSODm polypeptide which will be processed by the cellular amino-terminal processing enzymes resulting in removal of the methionine. The removal of the N-terminal methionine reduces the likelihood of an immunogenic reaction when the recombinant DNA product is administered to a human subject.

If desired, the hSODm gene may be joined to signal sequences, secretory leader and processing signals, to provide for secretion and processing of the hSODm. Various secretory leader and processing signals have been described in the literature. See for example, U.S. Pat. Nos. 4,336,336 and 4,338,397, as well as copending application Ser. Nos. 522,909, filed Aug. 12, 1983 and 488,857, filed Apr. 26, 1983, the relevant portions of which are incorporated herein by reference.

Of particular interest as hosts are unicellular microorganism hosts, both prokaryotes and eukaryotes, such as bacteria, algae, fungi, e.g. yeast, etc. In particular, *E. coli, B. subtilis, S. cerevisiae, K. lactis*, Streptomyces, and Neurospora may afford hosts.

A wide variety of vectors are available for use in unicellular microorganisms, the vectors being derived from plasmids and viruses. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers are present, which provide for different characteristics.

In addition to the markers, vectors will usually have a replication system and in the case of expression vectors, will usually include both the initiation and termination transcriptional regulatory signals, such as promoters which may be single or multiple tandem promoters, an mRNA capping sequence, a TATA box, enchancers, terminator, polyadenylation sequence, and one or more stop codons associated with the terminator. For translation, there will usually be a ribosomal binding site for prokaryotes, as well as one or more stop codons, which may be provided by the vector or by the structural gene. Alternatively, these regulatory sequences may be present on a fragment containing the structural gene, which is inserted into the vector.

Usually, there will be one or more restriction sites conveniently located for insertion of the structural gene into the expression vector. Once inserted, the expression vector containing the structural gene may be introduced into an appropriate host and the host cloned providing for efficient expression of hSODm.

In some instances, specialized properties may be provided for the vector, such as temperature sensitivity of expression, operators or activators for regulation of transcription, and the like. Of particular interest is the ability to control transcription by exogenous means, such as temperature, inducers, corepressors, etc., where transcription can be induced or repressed by an exogenous compound, usually organic.

In some instances integration of the expression system may be desirable. In that event that expression construct will usually involve a sequence homologous with DNA in a chromosome of the host. Frequently, the DNA may be a gene which provides prototrophy to an auxotrophic host or provides some other means for selection.

A number of expression systems have been developed for yeast which provide for constitutive or regulated expression. See, for example, EPA 83/306,507.1 and U.S. application Ser. No. 868,639 filed, May 29, 1986, whose disclosure is incorporated herein by reference.

Strong yeast transcriptional initiation regions include glycolytic enzyme initiation regions of genes such as glyceraldehyde-3-phosphate dehydrogenase, pyruvate kinase, alcohol dehydrogenase, phosphoglucoseisomerase, triose phosphate isomerase, phophofructokinase, etc., acid phosphatase, etc. Regulatory and/or enhancer regions may be joined 5' to the transcription initiation region, which regions may be obtained from UDP-galactose epimerase (GAL10), galactokinase (GAL1), acid phosphatase (PH05), alcohol dehydrogenase I and II, etc.

Where the hSODm is made intracellularly, when the cell culture has reached a high density, the cells may be isolated, conveniently by centrifugation, lysed and the hSODm isolated by various techniques, such as extraction, affinity chromatography, electrophoresis, dialysis, or combinations thereof. Where the product is secreted, similar techniques may be employed with the nutrient medium, but the desired product will be a substantially higher proportion of total protein in the nutrient medium than in the cell lysate.

The hSODm which is formed has substantially the same amino acid sequence as the naturally occurring human managanese superoxide dismutase, usually differing by no more than 5 amino acids, more usually differing by no more than 3 amino acids, and differing in one example by only 2 amino acids. The recombinant hSODm ("r-hSODm") displays substantially the same biological properties as naturally occuring hSODm. The biological properties include immunological properties, where antibodies raised to authentic hSODm cross-react with r-hSODm. Furthermore, in common bioassays employed for hSODm, the r-hSODm product demonstrates a substantial proportion, usually at least about 10%, preferrably at least about 50%, more preferably at least about 80%, of the enzymatic activity of the authentic hSODm, based on weight of protein. An illustrative assay technique is described by Marklund et al., *Eur. J. Biochem.* (1974) 47:469–474.

Human manganese superoxide dismutase was produced in bacterial cells using the plasmid containing the isolated hSODm gene. The activity of the superoxide dismutase in the bacterial cells was determined by polyacrylamide gel electrophoresis and staining for superoxide dismutase activity as described by Beauchamp et al. (1971). In Example III there is a comparison of the human superoxide dismutase produced in the bacterial transformant with human manganese superoxide dismutase, bacterial iron superoxide dismutase and a hybrid between the bacterial manganese and iron superoxide dismutase.

Yeast expression vectors for the production of the human manganese superoxide dismutase may be constructed beginning with the plasmid pC1/1 as described in the European patent application 116 201. Synthetic DNA linkers were constructed which had restriction sites with complementary ends to a restriction site in the plasmid pC1/1. These linkers were inserted into the plasmid using conventional ligation procedures. One such linker is shown in Example IV. These linkers are useful in providing unique restriction sites for constructing expression plasmids such as pC1/1XSS. The GAP regulatory regions were isolated from the plasmid pPGAP as described in European patent application 164556. The GAP promoter and the GAP terminator were isolated and combined using the restriction sites present in the linker inserted into pC1/1 XSS. The human manganese superoxide dismutase gene was inserted into the yeast expression vector pC1/1 XSS GAP using a linker described in Example IV. The resulting plasmid was pC1/1 XSS GAP hSODm which was used to transform the *S. cerevisiae* strain P017 which then expressed the human superoxide dismutase. Human superoxide dismutase activity produced in yeast is determined by the same procedures used for the bacterial expression system.

Human superoxide dismutase is useful in applications where superoxide dismutase is useful. It is particularly useful in human applications to prevent or minimize possible immune response. Human superoxide dismutase finds clinical use particularly as an anti-inflammatory agent and to minimize post-ischemic tissue injury.

Wilsmann, Procedings of the 4th International Conference on Superoxide and Superoxide Dismutase held in Rome, Italy, Sep. 1–6, 1985, ed. Rotilio pp 500–507 describes 10 years of clinical experience with SOD treatment of inflammatory disorders, particularly inflammatory joint disease. Flohe et al., pp 424–430 in Biological and Clinical Aspects of Superoxide and Superoxide Dismutase Developments in Biochemistry, v. 11(b), Bannister and Bannister, (eds.), 1980, describes clinical trials using superoxide dismutase to treat osteoarthritis of the knee joint. Both articles recognize that human SOD would be preferable to bovine SOD to prevent allergic/anaphylactic reactions in the patients.

Patients having inflammatory joint disease are treated by a weekly intraarticular injection into a joint afflicted with the disease of a solution having human manganese superoxide dismutase in a suitable diluent in an amount effective to reduce inflammation, usually 1 to 10 mg, more usually 2 to 6 mg. The injections are given weekly for a period of time sufficient to reduce inflammation, usually for 2 to 8 weeks, more usually for 4 to 6 weeks. Because the articular capsule limits leakage of the high molecular weight compound each afflicted joint should be treated with the required dosage.

hSOD is conveniently stored lyophilized with sugar, usually sucrose, usually in a ratio of 1:2 w/w. The lyophilized enzyme is conveniently reconstituted in a suitable diluent for the particular application. For example, to treat inflammatory joint disease hSOD may be reconstituted in physiologic saline in a volume convenient for intraarticular administration so that the required number of milligrams of hSOD are contained within 0.5 to 5 ml of solution.

hSOD is also useful to minimize post-ischemic tissue damage. Such damage occurs whenever perfusion of an organ is interrupted as by the presence of a clot, due to a heart attack, or where blood flow to an organ is interrupted during surgical procedures such as where blood supply to an organ is clamped off during organ transplant or other surgery. In such instances the patient is administered 10 mg to 1,000 mg, more usually 50 mg to 500 mg of human manganese superoxide dismutase in a suitable diluent during the isahemic reaction. When the patient suffers ischemia due to a disease the solution is administered intraveneously or intraarterially as a bolus dosage or a continuous infusion. In such situations the hSOD may be administered in conjunction with fibrinolytic agents such as fibrin, fibrinogen or tissue plasminogen activator (TPA).

When ischemic damage is due to a surgical procedure, hSOD is administered during surgery. This application finds particular use in organ transplant surgery where hSOD is preferably administered prior to reirrigation of the organ and is also useful in any other surgery where bloodflow to an organ is interrupted, such as open heart surgery.

EXPERIMENTAL

General Methods

Preparation of plasmid DNA and poly(A)+ RNA, restriction enzyme digestions, screening of cDNA and genomic libraries, agarose gel electrophoresis, and DNA blotting and hybridization were carried out by standard procedures as described by Maniatis et al, (1982) Molecular Cloning: Lab. Manual (CSH New York: CSH Labs). DNA sequencing was done by the dideoxy-chain termination method (Sanger et al., *J. Mol. Biol.* 143:161–178) with specific oligonucleotide primers (Sanchez-Pescador et al., *DNA* (1984) 3:339–343) after suboloning into bacteriophage M13 vectors (Messing, *Methods in Enzymology* (1983) 101:20–78). Synthetic oligonucleotides were synthesized as described in Warner et al, *DNA* (1984) 3:401–411).

Bacterial cells were transformed and grown in L Broth-ampicillin as described by Maniatis et al., (1982), supra. Yeast were transformed according to Hinnen et al., *Proc. Natl. Acad. Sci. USA* (1978) 75:1929–1933 and were grown using a variety of media including selective medium (yeast nitrogen base supplemented with amino acids, etc.) as appropriate but without leucine; yeast extract and peptone containing 2% (w/v) glucose (YEPD); and in the case of plating medium containing 2% (w/v) agar and for transformation 3% top agar.

Example I

Cloning of hSODm, cDNA and Amino Acid Sequence Determination cDNA Cloning

The cDNA clones encoding the human manganese SOD were isolated from an adult human kidney library in λgt10 (Huynh et al. 1985 "in DNA Cloning: A Practical Approach", Glover, D. H. ed. IRL Press Oxford, pp 49–78). Double-stranded cDNA was prepared essentially as described by Gubler et al., *Gene* (1983) 25:263–269 and after methylation of internal EcoRI sites and the addition of EcoRI linkers the cDNA was ligated into the EcoRI site of λgt10. Clones containing segments of the human manganese SOD were identified by hybridization with two chemically synthesized oligonucleotide probes. The sequence of the probes is shown below and was deduced from the amino acid sequence by Barra et al., *J.B.C.* (1984) 259:12595.

Probe 1:

5'-TTGTTCACGTAGGCGGCGTGGTGCTTG-GAGTGGTGCAGCTGCAT-3'

(complementary to mRNA that codes for amino acids 23–27 of the mature protein as numbered by Barra et al.)

Probe 2:

5'-GCCATGTATCTCTCGGTCACGTTCTC-CCAGTTGATCACGTTCCA-3'

(complementary to mRNA that codes for amino acids 197–211 of the mature protein as numbered by Barra et al.)

Probe 1 and Probe 2 were used to select those members of the λgt10 library that contained the hSODm gene. Probe 1 was specific for DNA coding for the hSODm amino acids 23 to 27, and Probe 2 was specific for DNA coding for the hSODm amino acids 197–211. Those library clones that hybridized with both Probe 1 and Probe 2 contained either a large fragment (equivalent to amino acids 23–211) or the complete hSODm gene. One of the isolates was a full-length clone (hMnSOD-4). This clone (hMnSOD-4) was selected for sequencing and expression.

Sequence of hSOD Mn

FIG. 4 shows the full nucleotide sequence determined for clone hMnSOD-4 and the deduced amino acid sequence. In parenthesis are indicated the EcoRI linkers used in the cloning procedure. When this amino acid sequence is compared to that reported by Barra et al. 1984 supra, two differences emerge. First, Barra et al. presented the sequence of the mature protein which has a lysine at the amino terminus. The sequence shown in FIG. 4 codes also for an additional 25 amino acids upstream from the lysine (which is in position 1, see FIG. 4). These amino acids correspond to a signal sequence that is cleaved to give rise to a mature protein. Second, there are two amino acids (Gly, Trp in positions 124, 125; underlined in FIG. 4) that are absent from the published amino acid sequence by Barra et al. 1984 supra. Therefore, the observed amino acid sequence is different from that previously reported.

Example II

Construction of a Bacterial Expression Vector for Serine hSOD Mn: Plasmid pNco5AHSODm (FIGS. 1a & b)

A bacterial expression vector was constructed which contains hSODm cDNA inserted after a mini-gene (coding for 4 amino acids). The two sequences are separated by a translational stop codon and they generate a polycistronic mRNA.

Plasmid pNco5AHSODm was constructed as follows. An EcoRI fragment of about 850 bp from lambda clone, hMnSOD-4, coding for the pre-SODm was excised by EcoRI digestion and purified by agarose gel electrophoresis. This fragment was ligated to ptac5 (Hallewell et al., *Nucleic Acids Res.* (1985) 13:2017) previously digested with EcoRI. The EcoRI site is present in the polylinker of ptac5. The ligation mix was used to transform *E. coli*. Several transformant colonies selected in ampicillin-L broth plates were screened by restriction analysis. One clone (ptac5HSODm) containing the correct orientation (3'-end near the SalI site on the polylinker) was selected for further manipulation.

Plasmid ptac5HSODm was digested with NarI which cuts in the hSODm cDNA sequences coding for amino acids 12–13. The NarI site is indicated with the double underlining in FIG. 4.

Synthetic linkers of the sequence described in FIG. 1 were ligated to linearized ptac5HSODm.

The linker provides for a NcoI overhang, a mini-gene coding for 4 amino acids which incorporates in its sequence a Shine-Dalgarno sequence for ribosome binding, a stop signal, an ATG for the first translation initiation methionine codon for hSODm and a sequence coding for ten amino acids of the hSODm.

The two first amino acids of the mature protein were not included in the synthetic linker (see FIGS. 1 and 4). Instead, the residue that is in third position in the mature protein (Ser) is adjacent to the Met in the linker sequence. This choice is made because bacteria and yeast process and cleave after methionine when followed by a serine (Tsunasawa et al., J.B.C. (1985) 260:5382). Therefore, a mature hSODm is obtained without an N-terminal methionine. If the initiating methionine is followed by Lys the first residue of the mature protein, the methionine would not be cleaved. In this case one would obtain a methionyl-hSODm which could be antigenic for human use because it contained an N-terminal methionine.

The ptac5HSODm with ligated linkers was digested with NcoI and SalI (which cuts after the 3'-end of the insert). The NcoI-SalI fragment (ca.715 bp) was gel purified. This fragment was cloned into NcoI-SalI digested pSODNco5A to yield pNco5AHSODm.

Figure 2:
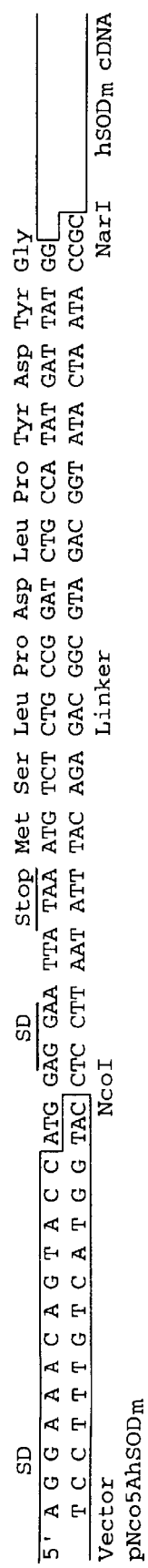
FIG. 2 shows the junction sequence between vector and insert and translation initiation sites for the mini-gene and hSODm in pNco5AhSODm.

Plasmid pNco5ASOD is a pBR322 derived bacterial expression plasmid for Cu/Zn hSOD. The plasmid contains the tac promoter and Cu/Zn hSOD cDNA as an EcoRI-SalI insert substituting pBR322 sequences between EcoRI and SalI. The tac promoter is proximal to the EcoRI site and the direction of transcription is clockwise. The tac promoter and hSOD cDNA insert of pSODNco5A was obtained from pNco5ASOD (Hallewell et al., supra). FIG. 2 shows the junction nucleotide sequence between vector and insert and translation initiation region of both mini-gene and hSODm. The figure indicates the source of the DNA sequences.

Example III

Expression of hSODm in Bacteria

Bacterial cells E. coli MC1061 (Casadaban et al., J. Mol. Biol. (1980) 138:179–207) or E. coli HB101 were transformed with plasmid pNco5AHSODm. The hSODm transformant cells were selected in L-broth plates containing 100 ug/ml of ampicillin. Cultures prepared in L-broth-amp containing 0.2 mM $MnCl_2$ were grown at 37° C. to late-log-phase with agitation.

Cells (1 ml) were harvested and lysed with glass beads as follows: Fifty ul of 2 mM $MnCl_2$, 35 mM $KPO_4$ pH 7.8, 1 mM PMSF were added to the cell pellet. In addition, 50 ul of acid washed glass beads were also added. The mixture was vortexed six times for 30 seconds each, leaving the tube 30 seconds on ice between vortexing. The mix was centrifuged for 30 seconds in an Eppendorf microfuge. The supernatant was saved and the pellet was discarded.

A sample of 10 ul of the supernatant was loaded onto a 10% native polyacrylamide gel electrophoresed and stained for SOD activity (Beauchamp et al., Anal. Biochem. (1971) 44:276–287.)

Results show that E. coli MC1061 or HB101 constitutively expressed hSODm. Several bands are detected on the activity gels of extracts of the bacterial tranformants. The bands correspond to the human manganese SOD, bacterial manganese SOD, bacterial iron SOD and a hybrid between bacterial manganese and iron SOD. The bacterial SOD forms have been previously described (Caroioz et al., EMBO. J. (1986) 5:623).

Figure 5:
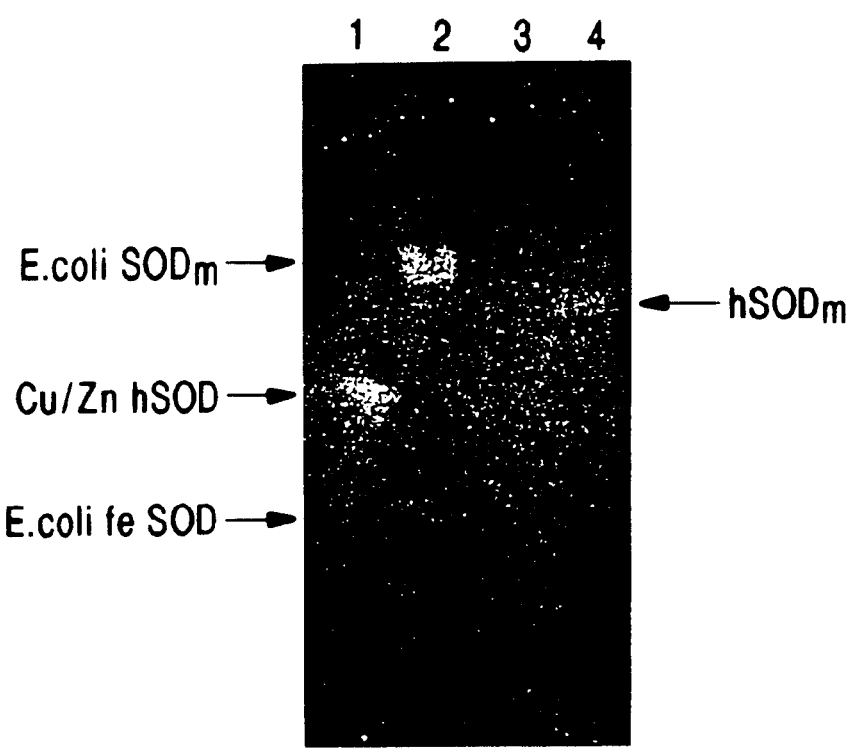
FIG. 5 is a picture of an SOD activity gel depicting expression of hSODm in bacteria.

In order to confirm the identity of the newly synthesized hSODm, plasmid pNco5AHSODm was transformed into E. coli cells QC774(SOD A⁻ SOD B⁻) (Caroioz et al., supra), which lack bacterial SOD. Extracts of these cells were prepared as above and electrophoresed on a 10% native acrylamide gel as previously described. FIG. 5 shows the activity gel. The first lane contains 0.4 µg of purified Cu, Zn human hSOD as activity control. Lane 2 contains extract of E. coli strain GL4468 (parent of the SOD⁻QC774 strain). Two bacterial SOD activity bands are detected corresponding to the following from top to bottom: E. coli $SOD_m$ and E. coli FeSOD. Lane 3 contains extract of E. coli strain QC774 transformed with pBR322 (negative control) and lane 4 contains extract of the same QC774 strain transformed with the SODm expression plasmid. The results clearly confirm that a new SOD activity band appears in the SOD⁻ mutants when transformed with the expression plasmid (lane 4). This band is not present in extracts of cells without plasmid (lane 3). The new band has a molecular weight of about 23,000 daltons as determined by Coomassie Blue staining of gels.

Example IV

Construction of Yeast Expression Vectors for hSODm

Construction of Plasmid pC1/1 XSS

Since some SODm contain a BamHI site in their sequence, it was necessary to engineer the yeast expression vectors (in which the cloning site for the expression cassette is a BamHI) to include other single sites. For this reason, two derivatives were constructed in which the single vector BamHI site was deleted and new SacI, SacII and XhoI (XSS) were introduced. Description of the construction of these derivatives is shown below.

Plasmid pC1/1 (see EPO 116 201) was linearized with BamHI and phosphatased. The synthetic DNA linkers of sequence shown below, having BamHI complementary ends and restriction endonuclease sites for SacI, SacII and XhoI were phosphorylated with T4 polynucleotide kinase. After removal of the kinase they were ligated to the linearized pC1/1. The BamHI is not reconstituted by ligation of this linker.

```
5' GATCG AGCT|CCC GC|GGC|TCGA GC 3'
   3'C|TCGA GGG|CG CCG AGCT|CGCTAG 5'
       SacI    SacII   XhoI
```

After transformation of the yeast strain MC1061 a recombinant plasmid was obtained which had the linker inserted at the BamHI site. SacI, SacII and XhoI are unique sites in pC1/1 XSS.

Construction of Plasmid pPGAPXSS

Plasmid pPGAPXSS is a derivative of pPGAP (EPO 164 556) in which the following linker was inserted at the junction between the GAP promoter and/or GAP terminator sequences and the vector sequences:

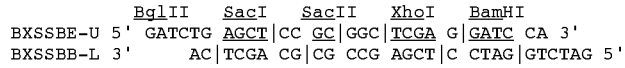

Figure 3A:
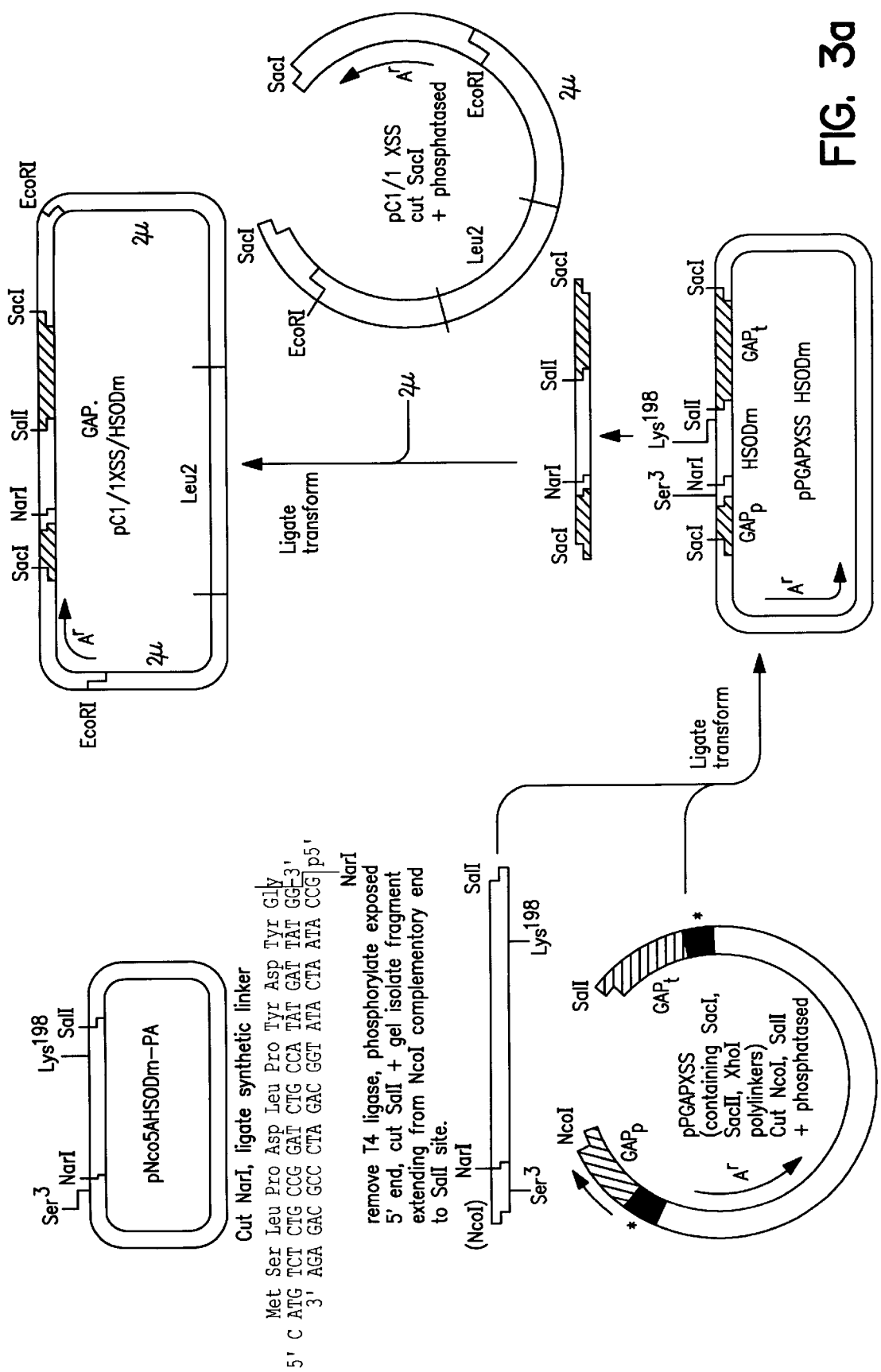
FIGS. 3*a* and 3*b* are a flowchart describing the construction of pC1/1XSShSODm, a yeast expression plasmid for hSODm.
Figure 3B:
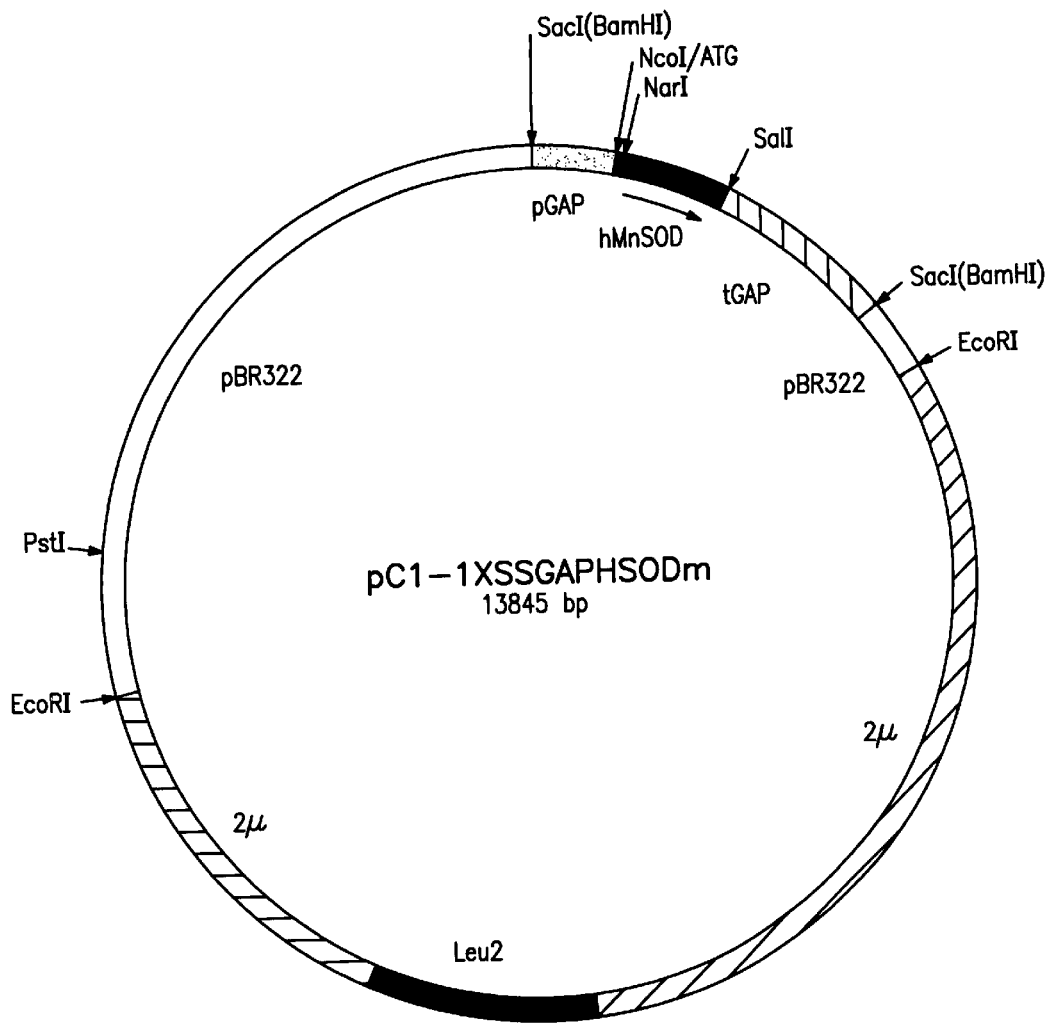

As FIG. 3 shows, the linkers provide for SacI, SacII, XhoI and BamHI adjacent to both, 5' end of GAP promoter sequences and 3' end of GAP terminator sequences. Both BamHI and BglII sites coming from pPGAP ends and linkers, respectively were not reconstructed.

Construction of Plasmid pC1/1XSSGAP hSODm
for Expression of hSODm in Yeast (FIGS. 3a & b)

In order to prepare yeast expression vectors for hSODm, the polyA sequences present at the end of the hSODm cDNA were removed.

To remove the polyA sequences from pNco5AHSODm, the plasmid was digested with PvuI which cuts upstream from the polyA tract as shown in FIG. 4. The overhang was filled in using the Klenow fragment of DNA polymerase I. The plasmid was subsequently digested with NcoI. A 615 bp fragment containing the hSODm cDNA was gel isolated and was re-inserted into pNco5AHSOD (see FIG. 1), digested with NcoI and SmaI (which cuts next to SalI, as indicated in FIG. 1) to yield pNco5AHSODm-PA, after transformation of E. coli MC 1061.

Plasmid pNco5HSODm-PA (see FIG. 3) is linearised with NarI and ligated to the synthetic DNA linker shown below. The lower strand of the linker is phosphorylated in this ligation.

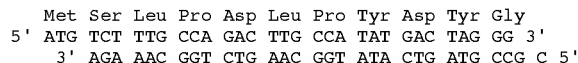

Following ligation, the plasmid is cut with SalI and the about 720 bp linker to SalI fragment is isolated by preparative agarose gel electrophoresis. This fragment is ligated to NcoI and SalI cut PPGAPXSS in the presence of NcoI. After transformation of MC1061 a colony containing the recombinant plasmid pPGAPXSS HSODm is obtained. This plasmid is cut with SacI and the ca. 2 kb fragment containing GAPp, hSODm and GAPt (p-promoter, t-terminator) isolated by preparative agarose gel electrophoresis and ligated to SalI cut and phosphatased pC1/1 XSS. A colony containing the recombinant pC1/1XSSGAPhSODm-PA plasmid with GAPP proximal to the ampicillin resistance gene was obtained. The plasmid DNA was prepared and used to transform yeast strain *Saccharomyces cerevisiae* P017 (Mata, leu 2–04, cir°), selecting for colonies on agar plates lacking leucine.

Example V

Expression of hSODm in Yeast

Cultures are grown in 1 ml Leu⁻ medium to saturation and 1 μl of this culture was added to 1000 μl YEPD+0.2 mM $MnCl_2$ and grown to saturation. Cells are harvested, lysed with glass beads, and the equivalent of 0.5 $OD_{650}$ units of cells loaded on a native SOD activity gel to determine activity.

Example VI

Treatment of Patients with hSODm

Methods for treating patients with hSODm are similar to methods for treating patients with bovine SOD except that hSOD is expected to be somewhat more effective and may be capable of being used in reduced amounts or for shorter periods of time.

Inflammatory Joint Disease Patients

Patients having osteoarthritis or rheumatoid arthritis have been treated by an intraarticular injection of 4 mg of bovine SOD and 8 mg of sucrose in 2 ml of normal saline in an affected joint for six weeks, as described in Flohe, supra. It is expected that 4 mg hSODm and 8 mg sucrose diluted in 2.0 ml normal saline will be effective when administered as a weekly intraarticular injection for four weeks.

Treatment of Patients Having Surgically Induced Ischemia

A solution containing 250 mg of hSOD and 500 mg sucrose in 500 ml physiologic saline is expected to minimize reperfusion organ damage when used to perfuse a donated kidney prior to irrigation of the kidney during kidney transplant surgery. Intravenous or intraarterial administration as a bolus dose or continuous infusion of 50 mg to 500 mg total per patient during or following surgery is also expected to minimize reperfusion tissue damage.

The above results demonstrate the successful isolation and manipulation of the human manganese superoxide dismutase coding sequence, its replication in microorganisms, its manipulation to provide expression constructs for both prokaryotes and eukaryotes, particularly microorganism hosts, and the expression of functional human manganese superoxide dismutase in foreign hosts. Thus, a stable reproducible supply of human manganese superoxide dismutase is provided. In addition, contructs are manipulated to ensure that the superoxide dismutase is free of the additional methionine initiation codon which is not found in natural human manganese superoxide dismutase. High yields of the enzyme may be obtained in cultures substantially free of materials which might have an adverse effect when the subject enzyme is employed therapeutically.

Although the foregoing invention has been described in some detail by way of illustration and example for purposes of clarity of understanding, it will be obvious that certain changes and modifications may be practiced within the scope of the appended claims.

What is claimed is:

1. An isolated polypeptide comprising the amino acid sequence depicted in FIG. 4.

2. An isolated polypeptide comprising the amino acid sequence of amino acids from –24 to 198 of FIG. 4, wherein said polypeptide is produced by expressing a nucleic acid sequence encoding the polypeptide in a bacterium.

3. A polypeptide according to claim 2, wherein said bacterium is *E. coli*.

4. An isolated polypeptide comprising the amino acid sequence of amino acids from –24 to 198 of FIG. 4, wherein said polypeptide is produced by expressing a nucleic acid sequence encoding the polypeptide in a yeast.

5. A polypeptide according to claim 4, wherein said yeast is *S. cerevisiae*.

* * * * *